(12) United States Patent
Margossian et al.

(10) Patent No.: US 9,278,110 B2
(45) Date of Patent: *Mar. 8, 2016

(54) ANTI-REGURGITATION AND/OR ANTI-GASTROOESOPHAGEAL REFLUX COMPOSITION, PREPARATION AND USES

(71) Applicant: UNITED PHARMACEUTICALS, Paris (FR)

(72) Inventors: Jonathan Albert Margossian, Paris (FR); Nicolas Pradeau, Tinteniac (FR); Yannick Fallourd, Rennes (FR)

(73) Assignee: UNITED PHARMACEUTICALS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/672,619

(22) Filed: Mar. 30, 2015

(65) Prior Publication Data

US 2015/0202225 A1 Jul. 23, 2015

Related U.S. Application Data

(63) Continuation of application No. 13/993,712, filed as application No. PCT/EP2011/073039 on Dec. 16, 2011, now Pat. No. 9,072,767.

(30) Foreign Application Priority Data

Dec. 17, 2010 (FR) ..................... 10 60691

(51) Int. Cl.

| A61K 36/00 | (2006.01) |
|---|---|
| A61K 31/732 | (2006.01) |
| A23L 1/0524 | (2006.01) |
| A23L 1/0526 | (2006.01) |
| A23L 1/0534 | (2006.01) |
| A23L 1/054 | (2006.01) |
| A23L 1/29 | (2006.01) |
| A23L 1/308 | (2006.01) |
| A61K 31/717 | (2006.01) |
| A61K 31/723 | (2006.01) |

(52) U.S. Cl.
CPC ............ *A61K 31/732* (2013.01); *A23L 1/0524* (2013.01); *A23L 1/0526* (2013.01); *A23L 1/0534* (2013.01); *A23L 1/0541* (2013.01); *A23L 1/296* (2013.01); *A23L 1/308* (2013.01); *A61K 31/717* (2013.01); *A61K 31/723* (2013.01); *A23V 2002/00* (2013.01)

(58) Field of Classification Search
None
See application file for complete search history.

(56) References Cited

U.S. PATENT DOCUMENTS

| 6,099,871 A | 8/2000 | Martinez |
|---|---|---|
| 2002/0193344 A1 | 12/2002 | Wolf et al. |
| 2003/0165606 A1 | 9/2003 | Lasekan et al. |
| 2004/0142017 A1 | 7/2004 | Luebbers |
| 2004/0228903 A1 | 11/2004 | te Hennepe et al. |
| 2004/0258825 A1 | 12/2004 | Ndife et al. |
| 2006/0078649 A1 | 4/2006 | Petermann et al. |
| 2007/0059429 A1* | 3/2007 | Wild et al. ............ 426/656 |
| 2007/1005942 | 3/2007 | Wild et al. |
| 2007/0224327 A1* | 9/2007 | Otte et al. ............ 426/577 |

FOREIGN PATENT DOCUMENTS

| FR | 2913857 | 9/2008 |
|---|---|---|
| RU | 2130728 C1 * | 5/1999 |
| WO | WO 01/56406 | 8/2001 |
| WO | WO 2010/046321 | 4/2010 |

OTHER PUBLICATIONS

Database WPI, Accession No. 2000-315804, May 27, 1999, XP-002670148.
Written Opinion in International Application No. PCT/EP2011/073039, Mar. 5, 2012, pp. 1-7.

\* cited by examiner

*Primary Examiner* — Qiuwen Mi
(74) *Attorney, Agent, or Firm* — Saliwanchik, Lloyd & Eisenschenk

(57) ABSTRACT

The invention relates to compositions intended for reducing, ideally for eliminating, regurgitation and/or gastro-oesophageal reflux phenomena affecting a subject. Anti-regurgitation and/or anti-reflux infant formulas and milks intended for feeding newborn babies, infants and young children are more particularly described.

9 Claims, 2 Drawing Sheets

ANTI-REGURGITATION AND/OR ANTI-GASTROOESOPHAGEAL REFLUX COMPOSITION, PREPARATION AND USES

CROSS-REFERENCE TO RELATED APPLICATIONS

This application is a continuation of U.S. Ser. No. 13/993,712, filed Jul. 30, 2013, which is the U.S. national stage application of International Patent Application No. PCT/EP2011/073039, filed Dec. 16, 2011.

The field of the present invention is that of medicine and human nutrition, and in particular infant nutrition.

The invention relates to compositions intended to reduce, ideally to eliminate, regurgitation and/or gastro-oesophageal reflux (GOR) phenomena affecting a subject, and also to the methods for obtaining them. Anti-regurgitation and/or anti-gastro-oesophageal reflux infant compositions, formulas, preparations and milks intended for feeding newborn babies, infants and young children are more particularly described.

Regurgitations constitute a symptom frequently observed in newborn babies and infants, resulting from an increase in abdominal pressure relative to thorax pressure. They often occur after meals or during eructation phenomena. These regurgitations, which can also affect adults, and differ, in the medical sense of the term, from vomiting, have no effect on the development of the child and are mainly a matter of discomfort.

The mechanism of regurgitations can be explained in the following way: the lower oesophageal sphincter is a circular muscle located in the lower part of the oesophagus. During meals, this muscle relaxes so as to facilitate the propulsion of the foods ingested (food bolus) into the stomach. The main function of this muscle is to prevent the return of the stomach contents towards the oesophagus by virtue of its tonic constriction.

In infants, this muscle may be immature. It may therefore not always support and compensate for the pressure exerted by the gastric content. It then has a tendency, during and after meals, to relax and to allow, during regurgitations, small amounts of gastric fluid to come back up into the pharynx and to the mouth, via the oesophagus.

This phenomenon generally appears from the first weeks of the child's life. The physiological development factors which contribute to the appearance of these regurgitations disappear, most commonly spontaneously, when the child reaches the age of 12 to 15 months (Vandenplas Y., Belli D. et al., Current concepts and issues in the management of regurgitation of infants: a reappraisal, Acta Pediatr 85: 531-534, 1996).

Regurgitations are often a cause of worry for parents who, as a result, do not hesitate to consult a physician. Concerns vary, in children, from simple discomfort, caused by the burping, to pain (since the oesophageal wall is irritated, this gives rise to oesophageal burns or even ulcers). This pain causes crying and often makes it complicated for the child to fall asleep.

In certain cases, excessively frequent and/or prolonged reflux may be responsible for complications defining, irrespective of the age of the subject affected, a pathological gastro-oesophageal reflux (GOR).

In infants and children in particular, pathological reflux can have more atypical oesophageal and respiratory consequences: a break in the weight/height curve, recurring rhino-pharyngo-bronchitis, asthma and bronchiolitis, or anaemia.

It is estimated that regurgitations and reflux occur in approximately 75% of children under the age of one.

The treatment recommended by the European Society of Paediatric Gastroenterology, Hepatology and Nutrition (ES-PGHAN) consists of a thickening of the food bolus. It has in fact been proven by clinical tests that an increase in the viscosity of the gastric content can significantly reduce the frequency and volume of regurgitations.

Drug therapies (prokinetics, antisecretory agents, etc.) are essentially reserved for recalcitrant regurgitations and especially for actual reflux.

Thickeners which have been conventionally used for a very large number of years, such as precooked and/or pregelatinized starches, carob seed flour or pectins, can be added to infant milk during the preparation of the feeding bottle.

Starches, in combination with proteins, caseins in particular, which flocculate at acidic pH, develop, in the stomach, the desired viscosity of the food bolus, which thus makes it possible to avoid regurgitations and reflux through a heaviness effect. The milk absorbed, at neutral pH in the feeding bottle, exerts, however, a buffering effect on gastric acidity, which effect is responsible for slowing down the thickening desired. The effectiveness of the starches then depends on the ability of the subject's stomach to acidify its food, i.e. to reduce the pH from approximately 7 to approximately 3, as rapidly as possible. In children, the required acidification can need between 30 and 60 minutes or more, during which time the child is not shielded from the regurgitations and reflux against which it is desired to protect it.

Contrary to starches, the effect of which depends on the stomach pH, carob seed flour (also referred to as "carob bean gum", "native carob", "standard carob" or "natural carob") is able to thicken at neutral pH. However, thickening the milk in the feeding bottle has the drawback, not insignificant for the child, of making the milk difficult to drink through the teat. The thickening of the milk in the feeding bottle can consequently be responsible for aerophagia problems.

A medicament, which has been known for several decades, and which is sold in pharmacies under the name Gelopectose®, is moreover used to thicken the contents of the stomach and the faeces. This medicament, consisting of pectin, microcrystalline cellulose and hydrated colloidal silica, is in the form of a powder to be poured into a feeding bottle of very hot (50 to 60° C.) reconstituted milk. The instructions for use of the medicament recommend vigorously shaking the feeding bottle, for approximately 30 seconds, and then leaving the mixture to stand for a few minutes until a gel and the desired temperature (approximately 37° C.) are obtained.

Although it has been used for several decades, this technique is not satisfactory. It is in fact lengthy and requires a heating means. In addition, the dosage of the powder added (2 level teaspoons ("cuillères à café") for 90 ml of water before reconstitution of the milk) is often imprecise.

The main drawback encountered with this medicament is the same as that encountered with the carob seed flour, and is linked to the thickening of the mixture in the feeding bottle. This thickening is in fact responsible for the formation of lumps which, very frequently, block the teat. Moreover, the texture of the reconstituted product changes over time and means that the preparation has to be consumed rapidly.

Since the approach previously described, consisting of adding a thickener to the feeding bottle of milk, proves to be not very practical, prethickened infant milks, termed "anti-regurgitation" (AR) milks, have moreover been proposed for several years.

These AR formulations already contain a thickener, chosen from starches and native carob bean gum, responsible for the viscosity of the reconstituted milk, and make it possible to overcome some of the drawbacks described above.

Native carob bean gum is a carob which has a low solubility in an aqueous medium of about 20% at a temperature between 10° C. and 45° C. (cf. patent application FR 2 913 857). The expression "solubility in an aqueous medium at a temperature between 10° C. and 45° C." means that, at a temperature between 10° C. and 45° C., in an aqueous medium, the carob bean gum produces at least 20% of the viscosity that it would have produced if it had been placed in solution at temperatures above 80° C.

Native carob and starches thus do not exhibit, at the reconstitution temperature of the milk in the feeding bottle (which is between approximately 30° C. and 50° C.), a satisfactory solubility in an aqueous medium. Since such a solubility is, however, necessary and a prerequisite for any homogeneous increase in viscosity, thickeners which are at least partially, or even completely, soluble at the reconstitution temperature of the feeding bottle are preferentially used by anti-regurgitation infant milk manufacturers.

In order to meet this need, ingredients and additives, such as precooked or pregelatinized starches and also "cold-soluble" carobs, a large proportion of the viscous potential of which is already expressed between 30 and 50° C., have been developed.

"Cold-soluble" carob bean gum is a carob which has a solubility in an aqueous medium of greater than 60% at a temperature between 10° C. and 45° C. according to the definition given above.

The ability of "cold-soluble" carobs to cause a rapid increase in the viscosity of the liquid milk base makes it, however, complicated and in practice impossible to apply certain technological treatments, such as a heat treatment (during the pasteurization or sterilization step), homogenization and atomization (spraying) necessary for the production of food powder, in particular powdered infant milks.

The same is true for precooked or pregelatinized starches, the structure of which is not very resistant to the high shear stresses to which the liquid milk base is subjected during the homogenization and atomization steps. The breaking up of the starch structure leads to a considerable or even total loss of the final viscosity of the reconstituted AR milk.

Starches, just like "cold-soluble" carob, can therefore only be added to the infant milk powder by dry mixing.

A major problem posed by the dry mixing of starch and/or of cold-soluble carob with the conventional constituent ingredients of an infant milk base concerns, however, the homogeneity of the final product. The relatively small amounts of carob flour or of precooked and/or pregelatinized starch to be added to the powdered infant milk base and the differences in physical properties of the two powders to be mixed in fact notably complicate the production of a homogeneous final product.

Processes for preparing liquid anti-regurgitation infant milk with a low dry matter content (between 11% and 15% by weight), involving a "UHT" (Ultra High Temperature) treatment, have moreover been described (see, for example, patent EP 0 611 525 B1 or FR 2 699 370 A1), but are not suitable for infant milk bases of which the dry matter content (before drying) is high, namely greater than 15% by weight, typically greater than 20% by weight, in particular greater than 25% or than 35% by weight, essentially because of an excessive viscosity which prevents a heat treatment, homogenization and/or atomization step from being correctly carried out.

In addition to the problems encountered, during the manufacture of infant milks, for obtaining a viscosity suitable for consumption of said milk by children suffering from regurgitation and/or GOR problems, manufacturers are, moreover, confronted with the need to produce a milk which meets the regulatory hygiene standards, the bacteriological criteria of which are strict.

While the pasteurization of AR infant milks which are in a liquid form poses little problem, this is not the case for AR infant milks which are in powder form. Thus, although infant milk powders have a low moisture content and a low water activity (Aw), and are packaged under a very low partial oxygen pressure, the bacteriological risk is still present and increased as long as ingredients are added via a dry mixing phase without the possibility of subsequent heat treatment.

Although regurgitation and reflux problems have been recognized for a long time, no entirely satisfactory anti-reflux and/or anti-regurgitation composition has been proposed to date.

The inventors describe, for the first time, an anti-regurgitation and/or anti-reflux composition (the expressions "anti-gastro-oesophageal reflux" and "anti-reflux" being used without distinction in the present text) in powder form, in particular an infant milk, and also effective methods for preparing such an infant milk.

SUMMARY OF THE INVENTION

The present invention thus relates to a composition, in particular an anti-regurgitation and/or anti-reflux composition, which is in the form of a powder, in particular a dietary or nutritional composition, preferably a milk, in particular an infant milk, preferably an anti-regurgitation and/or anti-reflux infant milk, comprising i) at least one weakly esterified pectin, preferably an amidated and weakly esterified pectin, and ii) at least one thickener and/or one gelling agent chosen, for example, from xanthan gum, carboxymethylcellulose, hydroxypropylcellulose, hydroxymethylcellulose, a carrageenan, an alginate, guar gum and carob seed flour, preferably chosen from xanthan gum, carboxymethylcellulose, hydroxypropylcellulose, hydroxymethylcellulose, methylcellulose, hydroxypropylmethylcellulose and guar gum, even more preferably from xanthan gum, carboxymethylcellulose and a mixture of xanthan and carboxymethylcellulose. This composition may advantageously also comprise iii) a highly esterified pectin.

The compositions in powder form according to the invention have the considerable and unexpected advantage of being, once reconstituted, i.e. obtained using a defined volume of water, liquid at pH 7, in particular in a feeding bottle, and already sufficiently viscous in the stomach, at a pH between 6 and 3.5, in particular between 5.8 and 5, and typically between 5.5 and 5, so as to significantly reduce or even eliminate regurgitation and/or reflux symptoms.

A particular subject of the invention relates to a drink which is reconstituted, for example a reconstituted milk, in particular an infant milk, from a composition, preferably from an anti-regurgitation and/or anti-reflux composition, in the form of a powder according to the invention.

Another particular subject of the invention relates to a liquid concentrate obtained from such a composition in powder form according to the invention.

The present invention also relates to a process for obtaining a composition in powder form, in particular an anti-regurgitation and/or anti-reflux composition in powder form, as described previously, in particular a pasteurized composition in powder form.

This process comprises the following steps of:

a) preparing a liquid base, the dry matter content of which is at least 20% by weight, by mixing, with stirring, at a temperature of at least 60° C., the constituent elements of said base,
b) homogenizing said base obtained at the end of step a) by fractionation of the constituent elements during a first step i) carried out at a pressure between 100 and 300 bar and during a step ii) carried out at a pressure between 10 and 60 bar,
c) spray-drying the mixture obtained at the end of step b), and
d) recovering the composition obtained at the end of step c) in powder form.

The previous process may also comprise a step of applying, to the liquid base obtained at the end of step a) or at the end of step b), a heat treatment, at a temperature between 60° C. and 110° C., for a period of time sufficient to pasteurize said base.

The composition according to the invention is preferably a dietary food for special medical purposes, in particular an infant milk, preferably an anti-reflux and/or anti-regurgitation infant milk, and the liquid base is preferably a liquid base of a dietary food for special medical purposes, in particular an infant milk liquid base.

The constituent elements of the composition preferably comprise at least one weakly esterified pectin, preferably at least one amidated and weakly esterified pectin, and at least one thickener and/or one gelling agent chosen, for example, from xanthan gum, carboxymethylcellulose, hydroxypropylcellulose, hydroxymethylcellulose, a carrageenan, an alginate, guar gum and carob seed flour, preferably chosen from xanthan gum, carboxymethylcellulose, hydroxypropylcellulose, hydroxymethylcellulose, methylcellulose, hydroxypropylmethylcellulose and guar gum, even more preferably from xanthan gum, carboxymethylcellulose and a mixture of xanthan and carboxymethylcellulose. A particularly preferred composition also comprises at least one highly esterified pectin.

A particular process according to the invention, for obtaining a pasteurized infant milk, comprises the following steps of:

a) preparing an infant milk liquid base, the dry matter content of which is at least 20% by weight, by mixing, with stirring, at a temperature of at least 60° C., the constituent elements of said base, said constituent elements comprising at least one amidated and weakly esterified pectin, xanthan and at least one highly esterified pectin,
b) homogenizing the infant milk liquid base obtained at the end of step a) by fractionation of the constituent elements during a first step i) carried out at a pressure between 100 and 300 bar and during a step ii) carried out at a pressure between 10 and 60 bar,
c) applying, to the infant milk liquid base obtained at the end of step a) or at the end of step b), a heat treatment at a temperature between 60° C. and 110° C. for a period of time sufficient to pasteurize said base,
d) spray-drying the mixture obtained at the end of step c), and
e) recovering the infant milk, said infant milk being typically a pasteurized anti-reflux and/or anti-regurgitation infant milk, obtained at the end of step d) in powder form.

The composition according to the invention is advantageously a composition which can be obtained using a process according to the present invention.

DETAILED DESCRIPTION OF THE INVENTION

The composition according to the invention may be a nutritional or dietary composition, in particular a dietary food for special medical purposes (FSMP), for example an infant formula or an infant milk, preferably an anti-reflux and/or anti-regurgitation infant milk. The infant milk may be a milk for infants (usable from birth), a follow-on milk (for babies aged at least six months) or a growing-up milk (for children at least one year old).

The composition according to the invention may also be a thickening preparation, typically an anti-reflux and/or anti-regurgitation preparation, intended to be added to a food (for children or adults) or else a pharmaceutical composition for preventing or treating a subject showing regurgitation or gastro-oesophageal reflux symptoms.

Conventionally, the subjects concerned are mammals, typically human beings of any age, preferably newborn babies, infants, for example babies aged 6 months or less, babies from 6 to 18 months old, or young children (children from 12 months to three years old). The subjects concerned may also be children over the age of three, adolescents or adults.

The composition according to the invention, typically the anti-regurgitation and/or anti-reflux composition according to the invention, is advantageously in the form of a powder to be reconstituted, i.e. to be dissolved in a drink (or in any consumable liquid), typically water or milk, for example cow's milk or goat's milk, before ingestion by the subject exhibiting regurgitation and/or reflux symptoms or liable to exhibit said symptoms.

One particular subject of the invention relates to a reconstituted drink, preferably a reconstituted anti-regurgitation and/or anti-reflux drink, such as a drink at neutral pH, for example a milk reconstituted from a composition according to the invention which is in powder form.

Typically, an anti-regurgitation and/or anti-reflux liquid infant milk according to the invention comprises a content of said powdered infant milk of from 11% to 15% by weight and preferably of 13% by weight.

Another particular subject of the invention relates to a liquid concentrate (prepared from a composition, preferably an anti-regurgitation and/or anti-reflux composition, in powder form according to the invention) which is capable of being diluted, preferably using a liquid, the pH of which is close to neutral.

Typically, an anti-regurgitation and/or anti-reflux milk according to the invention in the form of a liquid concentrate, prepared from a composition in powder form according to the invention, comprises a content (i.e. a percentage of dry matter) of said infant milk of from 25% to 50% by weight and preferably of 35% by weight. Such a milk may be diluted so as to obtain liquid infant milk according to the invention, typically an anti-regurgitation and/or anti-reflux infant milk, comprising a content of said powdered infant milk of from 11% to 15% by weight and preferably of 13% by weight.

The concentrated infant milk is advantageously preserved by autoclave sterilization and preferentially by a UHT heat treatment followed by aseptic packaging.

The milks according to the invention may be administered orally or enterally. They are preferentially administered orally, since they have, in addition to their role as a food, essentially the role of preventing, limiting or even suppressing regurgitation and/or reflux symptoms.

The composition in powder form according to the invention in fact has the significant advantage of being, once reconstituted, liquid at pH 7 and viscous at a pH of between 6 and 3.5. It can therefore be used as an anti-regurgitation and/or anti-reflux composition.

For the purposes of the present invention, the viscosity of the food bolus is considered to be satisfactory if it makes it possible to reduce, and ideally eliminate, regurgitation and/or reflux symptoms.

The viscosity can be measured with a Brookfield viscometer, with a disc- or cylinder-shaped module and at rotational speeds of between 20 and 100 revolutions per minute. It is also possible to measure the flow time of a constant volume of product through a calibrated orifice.

Advantageously, the diluted or reconstituted compositions according to the invention have:

at a pH between 7.3 and 6.5, a viscosity between 20 and 50 centipoises (i.e. between 20 and 50 mPascal·second$^{-1}$), for example between 20 and 45 centipoises, between 20 and 30 centipoises or between 20 and 40 centipoises, preferably between 20 and 30 centipoises;

at a pH below 6.5, typically of 6 or below 6, typically between 5.8 and 3.5, in particular between 5.8 and 5 or between 5.5 and 3.5, and preferably between 5.5 and 5 (for example 5.4, 5.3, 5.2 or 5.1), a viscosity between 150 and 500 centipoises, for example between 150 and 250, 200 and 300 or 200 and 400, or between 250 and 350, preferably between 150 and 250 centipoises or between 200 and 250 centipoises.

One particular subject of the invention relates to a composition, preferably an anti-regurgitation and/or anti-reflux composition, in particular a dietary or nutritional composition, in particular a dietary food for special medical purposes (FSMP), for example a milk, preferably an infant milk, even more preferably an anti-reflux and/or anti-regurgitation infant milk, which is in the form of a powder, comprising at least one weakly esterified pectin, preferably at least one amidated and weakly esterified pectin, and at least one thickener and/or one gelling agent chosen, for example, from xanthan gum, carboxymethylcellulose, hydroxypropylcellulose, hydroxymethylcellulose, methylcellulose, hydroxypropylmethylcellulose, a carrageenan, an alginate, guar gum and carob seed flour, preferably from xanthan gum, carboxymethylcellulose, hydroxypropylcellulose, hydroxymethylcellulose, methylcellulose, hydroxypropylmethylcellulose, guar gum and a mixture of two or more, for example three, of said thickeners, even more preferably from xanthan gum, carboxymethylcellulose and a mixture of xanthan and carboxymethylcellulose.

Mixtures of thickeners which are preferred may be chosen from xanthan gum and carboxymethylcellulose, xanthan gum and hydroxypropylcellulose, xanthan gum and guar gum, xanthan gum and hydroxypropylmethylcellulose, xanthan gum and methylcellulose, xanthan gum, guar gum and carboxymethylcellulose, carboxymethylcellulose and guar gum, carboxymethylcellulose and hydroxypropylmethylcellulose, carboxymethylcellulose and methylcellulose, hydroxymethylcellulose and methylcellulose, and methylcellulose, guar gum and hydroxymethylcellulose, preferably from xanthan gum and carboxymethylcellulose, xanthan gum and guar gum, xanthan gum and hydroxypropylcellulose, and xanthan gum, guar gum and carboxymethylcellulose.

A milk reconstituted from a milk in powder form according to the invention, typically from an anti-regurgitation and/or anti-reflux milk in powder form according to the invention, has a particularly suitable viscosity from pH 6, and more generally at a pH of between 6 and 5, for example between 5.8 and 5.5, typically at a pH of 5.2, 5.3, 5.4, 5.5, 5.6 and 5.7.

It is therefore easy to drink via the teat of the feeding bottle and makes it possible for the subject to feed without frustration while at the same time limiting the risks of aerophagia of said subject. It develops, moreover, more rapidly than the known anti-regurgitation milks (a few minutes (typically between 5 and 10 minutes), preferably 5 minutes, compared with approximately 30 to 60 minutes), the desired viscosity in the stomach so as to limit or even eliminate regurgitation and/or reflux (GOR) symptoms. The pH required for the development of a satisfactory viscosity for the purposes of the invention is therefore significantly higher, for the composition according to the invention, than the required pH of approximately 3.5 for the known AR compositions.

The desired optimum viscosity of the anti-regurgitation and/or anti-reflux infant milk according to the invention is preferably less than 50 mPa·s-1, measured at a pH close to neutral and at a temperature between 35° C. and 40° C., and greater than 160 mPa·s-1, preferably at 200 centipoises, even more preferentially between 200 and 300 centipoises, when it is measured at pH=5.5 and at a temperature also between 35° C. and 40° C.

The constituent elements of the compositions according to the invention constitute the mixture identified in the context of the present invention by the term "base".

Typically, the constituent elements of the dietary or nutritional compositions according to the invention constitute the mixture identified in the context of the present invention by the term "dietary or nutritional composition base" and the constituent elements of the infant milks constitute the mixture identified in the context of the present invention by the expression "infant milk base".

An anti-regurgitation and/or anti-reflux infant milk according to the present invention may comprise any infant milk base known to those skilled in the art. Thus, any infant milk base, the nutritional properties of which are suitable for the needs of infants and children, including dietary foods for special medical purposes (FSMPs), can be used for preparing an infant milk according to the present invention.

A standard infant milk base comprises carbohydrates, lipids, proteins, minerals, vitamins and, optionally, growth factors. The usual proportions of these various constituents in the milk base are approximately 55% for the carbohydrates, 25% for the lipids, 15% for the proteins and 5% for the minerals and vitamins together, the percentages being calculated relative to the total weight of dry matter of the dehydrated milk base.

The milk base may also optionally comprise other compounds known to those skilled in the art, such as compounds for improving the texture of the milk, the taste of the milk and/or having a specific nutritional or functional interest (nucleotides, probiotics, prebiotics, etc.).

Conventionally, the protein fraction of the infant milk base comprises two types of proteins: proteins of animal origin, in particular those derived from milk (casein and soluble proteins, also known as whey proteins), and proteins of vegetable origin. The protein fraction can, however, comprise only one of these two types of proteins.

The proteins of animal origin can originate, for example, from cow's milk, from goat's milk, from human milk, from camel's milk, from buffalo milk, from ass's milk and/or from mare's milk.

The proteins of vegetable origin may originate, for example, from rice, from soybean and/or from pea.

The proteins present in the infant milk base, used in the context of the present invention, may be whole or, conversely, totally or partially hydrolysed. The hydrolysed proteins preferably have a degree of hydrolysis of between approximately 5% and approximately 90%, preferably between approximately 5% and approximately 50%. The degree of hydrolysis corresponds to the number of peptide bonds broken by the hydrolysis. The higher this number, the greater the hydrolysis.

In one particular embodiment for the purposes of the present invention, the degree of hydrolysis of the hydrolysed proteins is between approximately 20% and approximately 50%, preferably between approximately 20% and approximately 40%.

The protein fraction may also comprise amino acids as a mixture. The amino acids as a mixture may be natural amino acids, synthetic amino acids or a mixture of natural amino acids and synthetic amino acids.

The amino acids as a mixture may constitute by themselves the protein fraction of the anti-regurgitation infant milk according to the present invention. They may also be present alongside hydrolysed proteins and optional nonhydrolysed proteins.

These hydrolysed proteins and/or amino acids as a mixture are more easily digested than nonhydrolysed proteins and make it possible to accelerate gastric emptying. A preferred composition according to the invention, in particular a preferred anti-regurgitation and/or anti-reflux composition, comprises hydrolysed proteins and/or amino acids as a mixture.

A particular composition according to the invention, typically a particular anti-regurgitation and/or anti-reflux composition, comprises a protein fraction containing a majority of hydrolysed proteins and/or of amino acids as a mixture.

Another particular composition according to the invention, typically another particular anti-regurgitation and/or anti-reflux composition, comprises a protein fraction containing a majority of nonhydrolysed proteins.

The lipids typically capable of being part of the composition of the infant milk according to the present invention may be chosen, for example, from milk fat, safflower oil, egg yolk lipids, olive oil, coconut oil, palm oil, soybean oil, sunflower oil, fish oil, oils derived from algae and/or from fungi, palm olein, medium-chain triglycerides, and esters of fatty acids chosen, for example, from arachidonic acid, linoleic acid, palmitic acid, stearic acid, docosahexanoic acid, eicosapentanoic acid, linolenic acid, oleic acid, lauric acid, capric acid, caprylic acid and caproic acid.

The carbohydrates capable of being part of the composition of the present infant milk (other than the thickeners described later in the present description) can be any sugar known to those skilled in the art to be suitable for human nutrition, typically infant nutrition. Typically, the carbohydrates may be chosen from lactose, maltodextrins or glucose syrup, sucrose, fructose and glucose.

Examples of mineral salts, of vitamins and of other nutrients optionally present in the anti-regurgitation infant milk according to the invention include vitamin A, vitamin B6, vitamin B12, vitamin D, in particular vitamin D3 (cholecalciferol), vitamin E, vitamin K, vitamin C, folic acid, thiamine, inositol, riboflavin, niacin, biotin, pantothenic acid, choline, calcium, phosphorus, iodine, iron, magnesium, copper, zinc, manganese, chlorine, potassium, sodium, selenium, chromium, molybdenum, taurine and L-carnitine.

In addition to the compatibility and stability considerations linked to the preparation processes described in the context of the present invention and to the conditions for storage of a milk according to the invention, the presence and the specific amounts of mineral salts and of vitamins optionally present may change slightly according to the population targeted (infants or children aged from 6 to 18 months, for example).

In the context of the present invention, the terms "pectin" and "pectic substance" are used without distinction. Pectic substances are acidic polysaccharide polymers. They are composed of a main chain consisting of 1,4-linked uronic acid monomers between which are inserted rhamnose molecules via 1,2 and 1,4 linkages responsible for the zig-zag shape of pectin macromolecules. These complex molecules have branches both at the uronic acids and at the rhamnose via molecules of galactan, rhamnan, etc., type.

There is a large variety of pectins, the origin of which is exclusively vegetable. Pectins are present in large amount in the pips and zests of redcurrants, apples, quinces and citrus fruit.

The "weakly esterified" pectins used in the context of the present invention are typically citrus fruit pectins.

The degree of amidation of the "amidated and weakly esterified pectin", present in the composition according to the invention, is between approximately 5% and approximately 30%, preferably between approximately 5% and approximately 20%, more preferentially between approximately 10% and approximately 20%.

Its degree of esterification, typically of methylation, is typically between approximately 20% and approximately 50%, preferentially between approximately 30% and approximately 50% and more preferentially between approximately 30% and approximately 40%.

When the composition according to the invention is an infant milk, the presence, in this composition, of at least one weakly esterified pectin, preferably of at least one weakly esterified, amidated pectin, makes it possible to obtain a reconstituted infant milk (reconstituted after dissolving the powder in water) which has a low viscosity, typically a liquid milk which has a viscosity between 20 and 50 centipoises at a pH close to neutral.

In the compositions according to the invention, typically in the anti-regurgitation and/or anti-reflux infant milks, the "weakly esterified pectin" is present at a concentration of between approximately 1% and approximately 10%, preferably between approximately 2% and approximately 8%, for example between approximately 3% and approximately 8%, even more preferably between approximately 3% and approximately 6%, and is typically 4%.

Advantageously, the concentration, in a composition according to the invention, of weakly esterified pectin and optionally of highly esterified pectin will be adapted to the nature and to the amount of the proteins optionally present in the composition.

Advantageously, the concentration, in a composition according to the invention, of weakly esterified pectin, in particular of amidated and weakly esterified pectin, will be all the higher, the richer said composition is in hydrolysed proteins and, conversely, this concentration will be all the lower, the richer said composition is in nonhydrolysed proteins.

In one particular composition according to the invention, the concentration of nonhydrolysed proteins is between approximately 13% and 14% and that of weakly esterified pectin is approximately 3%.

In another particular composition according to the invention, the concentration of amino acids as a mixture is between approximately 13% and 14% and that of weakly esterified pectin is approximately 4%.

The "highly esterified" pectins that can be used in the context of the present invention are typically citrus fruit pectins, in particular nonamidated citrus fruit pectins.

The inventors have discovered that such a "highly esterified pectin", used in combination with at least one "weakly esterified pectin", preferably with at least one "amidated and weakly esterified pectin", makes it possible to improve the stability of the anti-regurgitation and/or anti-reflux composition according to the invention (in particular the stability of the proteins) at an acid pH, i.e. at a pH below 4.

The degree of esterification, typically of methylation, of the "highly esterified pectin" present in the composition according to the invention is between approximately 50% and approximately 90%, preferably between approximately 50% and approximately 80%, more preferentially between approximately 60% and approximately 70%.

The stability index of said pectin at pH=4 is between 140-200, preferably between approximately 150 and approximately 190, more preferentially between approximately 165 and approximately 185. This index is a measurement by sedimentation (between 100 and 200) of the ability of the highly esterified pectin to protect nonhydrolysed proteins in an acidic medium.

In the compositions according to the invention, typically in the anti-regurgitation and/or anti-reflux infant milks, the "highly esterified pectin" is advantageously present at a concentration between approximately 0.1% and approximately 10%, preferably between approximately 0.1% and approximately 8%, more preferentially between approximately 1% and approximately 3%.

Preferably, the concentration of highly esterified pectin, in a composition according to the invention comprising at least one weakly esterified pectin, preferably at least one amidated and weakly esterified pectin, and at least one highly esterified pectin, will be all the higher, the richer said composition is in nonhydrolysed proteins, and, conversely, this concentration will be all the lower, the richer said composition is in hydrolysed proteins and/or amino acids as a mixture.

In one particular composition according to the invention, the concentration of nonhydrolysed proteins is between approximately 13% and 14%, that of weakly esterified pectin, typically that of amidated and weakly esterified pectin, is approximately 3%, and that of highly esterified pectin is between approximately 3% and 4.5% (typically 4%).

In one particular composition according to the invention, the concentration of highly hydrolysed proteins is between approximately 13% and 14%, that of weakly esterified pectin, typically that of amidated and weakly esterified pectin, is approximately 4%, and that of highly esterified pectin is zero or approximately 1%.

As previously indicated, the composition according to the invention, typically the anti-regurgitation and/or anti-reflux composition, comprises at least one weakly esterified pectin, preferably at least one amidated and weakly esterified pectin, and at least one thickener and/or one gelling agent chosen, for example, from xanthan gum, carboxymethylcellulose, hydroxypropylcellulose, hydroxymethylcellulose, methylcellulose, hydroxypropylmethylcellulose, a carrageenan, an alginate, guar gum and carob seed flour, preferably from xanthan gum, carboxymethylcellulose, hydroxypropylcellulose, hydroxymethylcellulose, methylcellulose, hydroxypropylmethylcellulose, guar gum and a mixture of two or more, for example three, of said thickeners (such as those identified in the present text), even more preferably from xanthan gum and carboxymethylcellulose.

One particular subject of the invention is a milk, preferably an anti-regurgitation and/or anti-reflux milk according to the invention, comprising, for 100 grams of dry matter, 0.5 to 10 grams, preferably between 3 and 8 grams, of pectins ("weakly esterified pectin" and/or "highly esterified pectin"), and from 0.5 to 8 grams, preferably between 0.5 and 4 grams, typically between 0.5 and 1.5 grams, of the thickener(s) and/or gelling agent(s) chosen.

Among the thickeners of vegetable origin present in the compositions according to the invention alongside the pectin(s), preferred thickeners and/or gelling agents are advantageously chosen from xanthan gum and carboxymethylcellulose. A thickener of which the use is particularly preferred is xanthan gum, also identified, in the context of the present invention, as "xanthan".

Xanthan is a branched polysaccharide which is conventionally used as a food additive under the code E415, obtained from the action of a bacterium, *Xanthomonas campestris*. It consists of a combination of four subunits: glucose, mannose, glucuronic acid and pyruvic acid.

The inventors have discovered that xanthan is a thickener which is perfectly suitable for use in a composition according to the invention, in particular in an infant milk, in combination with one or two of the pectins previously mentioned (on the one hand, "weakly esterified" and, on the other hand, "highly esterified"). The inventors have in particular demonstrated that such a combination makes it possible to obtain a composition which has a smooth appearance and is not gelled in an aqueous medium at a pH close to neutral, in particular at the pH of reconstitution of the feeding bottle of milk, and which has a homogeneous viscosity, in particular at a pH of 6 or below 6, preferably between 5.5 and 3.5, making it possible to limit, and ideally to eliminate, regurgitation and/or reflux symptoms thanks to the rapid obtaining of the desired viscosity.

The inventors have also noted the stabilizing effect, both in an acidic medium and in a neutral medium, exerted by the xanthan used in combination with one or two of the pectins previously mentioned on the composition according to the invention.

The compositions according to the invention may also comprise starch, in particular precooked or pregelatinized starch, preferably pregelatinized starch.

Starch is a mixture of 2 homopolymers, amylose and amylopectin, composed of D-anhydroglucopyranose (AGU) units, which belong to the polysaccharide family. The AGU units are linked to one another via $\alpha$-(1-4) linkages, generally characteristic of storage polysaccharides, and $\alpha$-(1-6) linkages which are responsible for branches in the structure of the molecule. These two homopolymers, which differ by virtue of their degree of branching and their degree of polymerization, are:

amylose, slightly branched with short branches, the molecular weight of which can be between 10,000 and 1,000,000 Daltons. The molecule is made up of from 600 to 1000 glucose molecules; and amylopectin or isoamylose, a branched molecule with long branches every 24 to 30 glucose units by means of $\alpha$-(1-6) linkages.

The molecular weight of starch is between 1,000,000 and 100,000,000 Daltons, and its level of branching is about 5%. The total chain can come to between 10,000 and 100,000 glucose units.

The ratio between the amylose and the amylopectin depends on the botanic source of the starch.

Pregelatinized starch is obtained by heating a suspension in water (starch milk). This suspension is unstable but, when heated, becomes viscous and translucent.

A particular milk, typically an anti-regurgitation and/or anti-reflux infant milk according to the present invention, the protein base of which consists, for example, of an extensive hydrolysate of animal or vegetable proteins (degree of hydrolysis between 20% and 30%), may advantageously comprise:

between approximately 1% and approximately 10%, preferably between approximately 1% and approximately 5%, even more preferentially between approximately 2% and approximately 4%, by weight percentage, of dry matter of weakly esterified pectin, between approximately 0.1% and approximately 10%, preferably between approximately 0.1% and approximately 8%, even more preferentially approximately 1% of weight of dry matter of highly esterified pectin, and between approximately 0.1% and approximately 2%, preferably between approximately 0.1% and approximately 1%, even more preferentially between approximately 0.5% and 0.9% of weight of dry matter of xanthan, relative to the total dry matter weight of milk.

Such a milk may also comprise between approximately 0.1% and approximately 10%, preferably between approximately 0.1% and approximately 5%, even more preferentially between approximately 0.1% and 2%, as weight percentage, of dry matter of pregelatinized starch.

Such proportions are favourable to increasing the viscosity of the milk under the conditions previously described.

The infant milk base used in the context of the present invention is conventionally in liquid form and typically comprises a dry matter content (dry extract) of approximately 25% to 60% by weight, preferably of approximately 30% to 50%, of approximately 30% to 40% by weight, or of approximately 25% to 45% by weight, even more preferentially of approximately 30% to 40% by weight or approximately 35% to 40% by weight.

The pectins and thickeners and/or gelling agents used in the context of the present invention may be in powder form or in the form of an aqueous solution. For the purposes of the invention, the expressions "aqueous medium" or "aqueous solution" denote respectively a medium or a solution which at least partially consists of water.

A particular anti-regurgitation and/or anti-reflux milk according to the invention which is in powder form advantageously comprises at least 94% of dry matter, preferably at least 95% of dry matter, even more preferably at least 98% of dry matter.

The present invention also relates to a process for obtaining a composition in powder form, in particular a dietary or nutritional composition as described previously, preferably an infant milk, even more preferably an anti-regurgitation and/or anti-reflux infant milk, as described previously.

This process comprises the following steps of:
a) preparing a liquid base, the dry matter content of which is at least 20% by weight, by mixing, with stirring, at a temperature of at least 60° C., the constituent elements of said base,
b) homogenizing said base obtained at the end of step a) by fractionation of the constituent elements during a first step i) carried out at a pressure between 100 and 300 bar and during a step ii) carried out at a pressure between 10 and 60 bar,
c) spray-drying the mixture obtained at the end of step b), and
d) recovering the composition obtained at the end of step c) in powder form.

The previous process makes it possible, contrary to the processes known to date, to simply and effectively prepare, from the constituent elements of a base, typically from an infant milk base which is in liquid form, a composition according to the invention, preferably an anti-regurgitation and/or anti-reflux composition, typically an anti-regurgitation and/or anti-reflux infant milk, which will be dried and converted into a powder. The powder obtained at the end of this process is homogeneous, contrary to the powders obtained by dry mixing previously described, and the liquid composition reconstituted from such a powder has the previously described viscosity properties required for limiting, ideally suppressing, regurgitation and/or reflux symptoms.

The composition in powder form according to the invention may advantageously be a pasteurized composition.

For the purposes of the present invention, pasteurization denotes a step of heat treatment which causes the destruction of the microorganisms considered to be pathogenic to the subject for whom the composition is intended, and more generally a decrease in the bacterial flora.

Conventionally, the heat treatment is carried out at a temperature between approximately 60° C. and approximately 110° C. for a period of time between approximately 15 minutes and a few seconds, for example approximately 25 or 30 seconds. Those skilled in the art are able to determine the period of time suitable for a given temperature which will make it possible to obtain the desired pasteurization without destroying the composition, its nutrient properties or its anti-regurgitation and/or anti-reflux properties. With regard to the milk in particular, a person skilled in the art is able to determine the conditions suitable for preserving the proteins and vitamins.

For milk, in particular infant milk, the maximum total flora tolerated must not exceed 1000 CFU (Colony-Forming Units) per gram of powder.

Among this flora, *Clostridium perfringens, Escherichia coli, Bacillus cereus, Listeria monocytogenes*, coagulase-positive staphylococci, salmonellae and enterobacteria (in particular *Cronobacter sakazakii*) are in particular considered to be pathogenic and should preferably be totally eliminated. The process according to the invention, previously described, makes it possible to eliminate all the bacteria (in particular the bacteria previously listed) that are pathogenic to humans, in particular children.

The process previously described may also advantageously comprise an additional step of applying, to the liquid base obtained at the end of step a) or at the end of step b), a heat treatment at a temperature between 60° C. and 110° C. for a period of time sufficient to pasteurize the liquid base. This process thus makes it possible to obtain a pasteurized composition, typically a pasteurized anti-regurgitation and/or anti-reflux composition, in powder form.

Such a composition does not have the microbiological risks (in particular with respect to *C. sakazakii*) observed during the dry mixing of an infant milk base with starch or carob powder.

One particular subject of the present invention thus relates to a process for obtaining a pasteurized composition, typically a pasteurized anti-regurgitation and/or anti-reflux composition, in powder form, in particular an infant milk or a dietary composition as previously described, comprising the following steps of:
a) preparing a liquid base, the dry matter content of which is at least 20% by weight, by mixing, with stirring, at a temperature of at least 60° C., the constituent elements of said infant milk base,
b) homogenizing the liquid base obtained at the end of step a) by fractionation of the constituent elements during a first step i) carried out at a pressure between 100 and 300 bar and during a step ii) carried out at a pressure between 10 and 60 bar,
c) applying, to the liquid base obtained at the end of step a) or at the end of step b), a heat treatment at a temperature between 60° C. and 110° C. for a period of time sufficient to pasteurize said base,
d) spray-drying the mixture obtained at the end of step c), and
e) recovering the pasteurized composition obtained at the end of step d) in powder form.

Step a) of preparing a liquid base comprises mixing, with stirring, the constituent components, ingredients or elements of interest, as previously described, of said base.

The preparation of a liquid mixture involves the dilution of each ingredient in water.

The ingredients (base of the composition, for example infant milk base or dietary composition base, and thickener(s)) can be mixed in the form of powders and subsequently placed in solution. They can also be mixed in the form of solutions. It is also possible to envisage adding one of the components in powder form to the other component which is in solution. In this case, it is preferable to keep the component in solution stirring during the mixing with the component in powder form in order to limit, ideally to prevent, the formation of agglomerates during the mixing.

Thus, the aqueous nature of the mixture obtained at the end of step a) may originate from the liquid form of the thickeners, from the liquid form of the base used and/or from the addition of water to the mixture of the products used in powder form.

A stirrer or a mixing unit, for example a mixing pump, a deflocculator, or a mixer equipped with a rotor/stator system, may advantageously be used to dissolve the various ingredients and to facilitate the obtaining of a homogeneous base.

The preferred use of a mixer of suitable shape and size also makes it possible to avoid the excessive incorporation of air into the liquid base, in particular the milk base.

Those skilled in the art will, moreover, be able to adapt the rotational speeds so as to reduce even further such an excessive incorporation of air into the liquid base.

Mixing step a) is preferably carried out at a temperature of at least 60° C., for example between approximately 60° C. and 90° C. or between approximately 60° C. and 80° C., even more preferentially between approximately 70° C. and 75° C. Typically, the temperature is 75° C.

In one preferred embodiment, the liquid base obtained at the end of step a) is kept stirring until the application of the homogenizing step, for example using a device as previously described.

The step of homogenizing the mixed, optionally pasteurized, liquid base obtained at the end of step a) of the process according to the invention enables the fractionation of the constituent elements of said base. The homogenization comprises two steps of compression intended to reinforce the stability of this base. The first fractionation step i) is preferably carried out at a pressure between approximately 100 bar and approximately 300 bar, the second step ii) preferably being carried out at a pressure between approximately 10 bar and approximately 60 bar.

This step is advantageously carried out on a two-stage homogenizer.

The homogenization pressure of the first stage of said homogenizer is thus typically between approximately 100 bar and approximately 300 bar, preferably between approximately 150 bar and approximately 300 bar, even more preferentially between approximately 170 bar and approximately 200 bar.

The homogenization pressure of the second stage is typically between approximately 10 bar and approximately 60 bar, preferably between approximately 30 bar and approximately 60 bar, even more preferentially between approximately 30 bar and approximately 40 bar.

The pasteurization step optionally present in the preparation process according to the invention provides for the application, to the mixture obtained at the end of step a) or at the end of the homogenizing step, of a heat treatment between approximately 70° C. and approximately 110° C., preferably between 70° C. and 100° C., between 75° C. and 100° C., between 75° C. and 95° C., between 80° C. and 95° C. or between 85° C. and 95° C., even more preferentially between 80° C. and 90° C., for a period of time sufficient to inactivate and destroy at least the microorganisms considered to be pathogenic (in particular *C. sakazakii*).

Typically, the heat treatment of the pasteurization step is applied for at least 2 minutes, and preferably at most 10 minutes, when the temperature is less than or equal to 80° C., for example between 75° C. and 60° C., and for at least 25 seconds, typically at least one minute, and preferably at most 5 minutes, when the temperature is greater than or equal to 85° C., for example between 85° C. and 100° C.

The treatment may also be applied for a period of time greater than 2 minutes, and preferably less than 10 minutes, when the temperature is 75° C., for a period of time between approximately 2 minutes and approximately 3 minutes when the temperature is 80° C., for a period of time between approximately 1 minute and approximately 2 minutes when the temperature is 90° C., for a period of time of approximately 1 minute when the temperature is 95° C., and of less than 30 seconds, typically less than 25 seconds, when the temperature is 100° C.

The pasteurized or unpasteurized mixture obtained at the end of the homogenizing step of the process according to the invention is advantageously spray-dried in order to obtain a composition (preferably an anti-regurgitation and/or anti-reflux composition) in powder form comprising, as previously explained, a dry extract of between 85% and 99%, preferably a dry extract of at least 94% or of at least 95%, even more preferentially of at least 98%.

The pasteurized or unpasteurized mixture obtained at the end of the homogenizing step of the process according to the invention is typically introduced at the top of a spray tower. The mixture is then "sprayed" (converted into an aerosol or mist) by means of a spray turbine or by injection at high pressure through one or more nozzles. The droplets thus formed are carried along and dehydrated by a stream of hot air, the temperature of which is typically between 160° C. and 240° C., preferably between 180° C. and 220° C. The droplets are dried to give a powder, before falling onto the lower walls of the apparatus. The powder-moist air separation is obtained, for example, by means of cyclone separators, the use of which is well known to those skilled in the art.

When it is desired to obtain a powdered composition according to such a process, the dehydration in the spray tower should preferably not be total. The residual moisture present in the powdered composition may, for example, be between 6% and 14% at the bottom of the chamber. This residual moisture allows a limited and controlled agglomeration of the particles, which results in the formation of granules with a porous structure.

The dehydration can then be finished off in additional devices of the fluidized-bed dryer type. The powder can then be cooled inside a vibro-fluidized bed.

It is also possible to prepare a powdered anti-regurgitation and/or anti-reflux composition according to the invention (typically an anti-regurgitation and/or anti-reflux composition allowing, for example, the reconstitution of a milk having the properties previously described, for example a milk which is liquid at a pH of approximately 7 and viscous at a pH between approximately 6 and approximately 3.5, in particular at a pH between 5.8 and 5) by dry mixing a base (collected in powder form at the spray tower outlet) with an ingredient of interest as previously described, typically at least one weakly esterified pectin, preferably at least one amidated and weakly esterified pectin, and at least one thickener and/or one gelling agent chosen, for example, from xanthan gum, carboxymethylcellulose, hydroxypropylcellulose, hydroxymethylcellulose, methylcellulose, hydroxypropylmethylcellulose, a carrageenan, an alginate, guar gum and carob seed flour, preferably from xanthan gum, carboxymethylcellulose, hydroxypropylcellulose, hydroxymethylcellulose, methylcellulose, hydroxypropylmethylcellulose, guar gum and a mixture of two or more, for example three, of said thickeners (such as those identified in the present text), even more preferably from xanthan gum and carboxymethylcellulose.

Other advantages and applications of the present invention will emerge on reading the examples which follow, which should be considered to be purely illustrative and nonlimiting.

FIGURE LEGENDS

EXAMPLES

Example 1

Formulation

Figure 1:
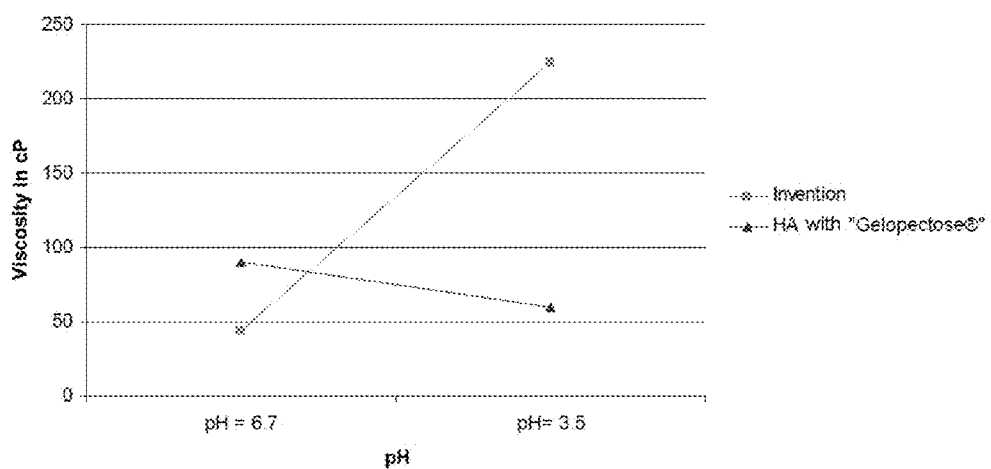
FIG. 1 represents the change in viscosity of the products (measured in centipoises cP) according to the pH of an infant milk prepared according to the present invention and of a hypoallergenic (HA) milk reconstituted with the addition of gelopectose. The x-axis of the graph therefore gives the pH values: 6.7 and 3.5, and the y-axis gives the viscosity values in centipoises.
Figure 2:
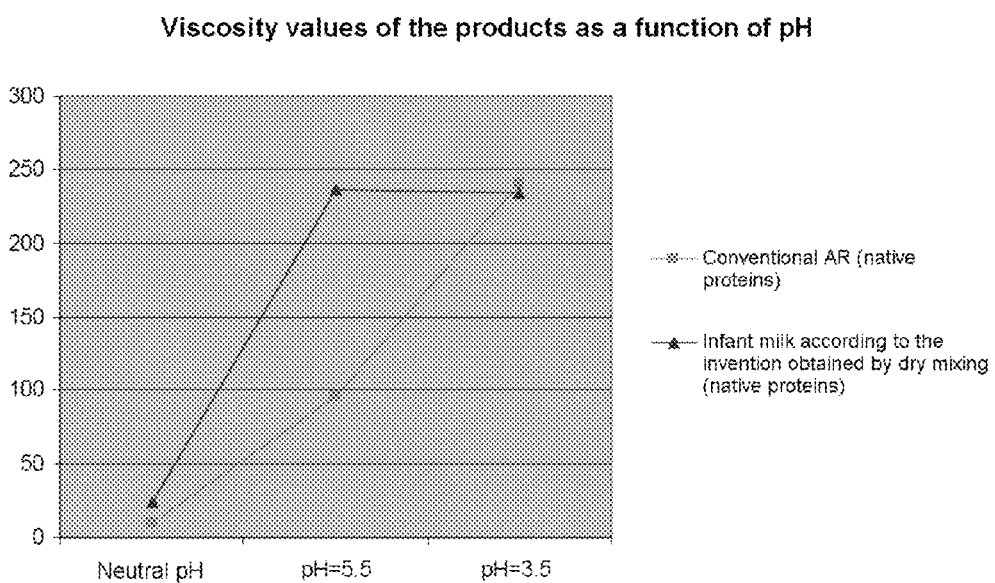
FIG. 2 represents the change in viscosity of the products (measured in centipoises cP) according to the pH of the infant milk reconstituted at 13% of dry extract. The x-axis of the graph therefore gives the pH values: neutral, 5.5 and 3.5, and the y-axis gives the viscosity values in centipoises.

The formulation of milks intended for feeding infants is most commonly strictly controlled by legislation which sets composition standards. Depending on the country, there may be differences in assessment owing in particular to local specificities in food diversification practice or else minor modifications of nutritional optimums resulting from work or studies carried out locally.

Under these conditions, the present example does not intend to represent the diversity of the thickened milk formulations according to the invention.

Conventionally, in order to meet the nutritional needs of infants, infant milks comprise approximately 10%-15% of proteins, approximately 25% of lipids and approximately 50% to 65% of carbohydrates, and also minerals, vitamins and, optionally, growth factors. Other ingredients, such as, for example, one or more prebiotics and/or probiotics, may moreover be added to infant milks.

An example of an anti-regurgitation and/or anti-reflux infant milk composition according to the invention is given in Table I below.

TABLE I

|   |   | For 100 g of powder | For 100 ml of reconstituted milk, at 13% |
|---|---|---|---|
| Proteins | g | 12.1 | 1.6 |
| Lipids, of which: | g | 26.2 | 3.41 |
| Linoleic acid | g | 4.5 | 0.6 |
| α-linolenic acid | mg | 450 | 58.5 |
| Carbohydrates, of which: | g | 52.7 | 6.85 |
| Maltodextrins | g | 46.85 | 4.0 |

TABLE I-continued

|   |   | For 100 g of powder | For 100 ml of reconstituted milk, at 13% |
|---|---|---|---|
| Lactose | g | 0 | 0 |
| Starch | g | 0.94 | 0.12 |
| HM pectin | g | 1.0 | 0.4 |
| LM amidated pectin | g | 4.0 | 0.52 |
| Xanthan | g | 0.7 | 0.09 |
| Energy | kcal | 495.9 | 64.5 |
| Minerals, of which: | g | 4.4 | 0.57 |
| Sodium | mg | 230 | 29.9 |
| Potassium | mg | 610 | 79.3 |
| Chlorine | mg | 340 | 44.2 |
| Calcium | mg | 620 | 80.6 |
| Phosphorus | mg | 340 | 44.2 |
| Magnesium | mg | 50 | 6 |
| Iron | mg | 6 | 0.8 |
| Zinc | mg | 4 | 0.52 |
| Iodine | µg | 70 | 9.10 |
| Copper | µg | 350 | 45.5 |
| Manganese | µg | 50 | 6.5 |
| Selenium | µg | 10 | 1.3 |
| Molybdenum | µg | <45 | <5.8 |
| Chromium | µg | <45 | <5.8 |
| Fluorine | µg | <980 | <127 |
| Mixture of vitamins | g | 0.3 | 0.039 |

Example 2

Process for Manufacturing a Pasteurized Infant Milk in Powder Form Comprising i) an Amidated and Weakly Esterified Pectin and ii) Xanthan The infant milk base comprising 40% of dry extract is prepared by mixing water previously heated to 75° C. with the various ingredients of the infant milk (proteins, amidated and weakly esterified pectins, carbohydrates, xanthan, minerals, vegetable fats, vitamins and growth factors). The pectins are incorporated into the infant milk base kept stirring in order to obtain complete dissolution thereof. The whole mixture is maintained at 75° C. with stirring in a jacketed tank until the homogenizing step. The infant milk base then undergoes double-stage homogenization at 200/40 bar, i.e. a first homogenizing step is carried out at a pressure of 200 bar and the second homogenizing step is carried out at a pressure of 40 bar. The homogenized infant milk base is then pasteurized by heat treatment at approximately 80° C. for 1 to 2 minutes for the purpose of eliminating the bacteriological risks, in particular those linked to Cronobacter sakazakii.

The pasteurized infant milk base then undergoes a spraying step carried out at a pressure of 160 bar, which makes it possible to obtain droplets which have a diameter sufficiently small to be dried with air, the temperature of which at the inlet into the chamber is 183° C. and the temperature of which at the outlet of the chamber is 94° C.

The process implemented makes it possible here to obtain a flow rate of 1000 and 2000 kg of powder/hour.

The reconstituted liquid milk (ready for consumption) obtained from this infant milk powder has a dry extract of approximately 13% in the feeding bottle. The viscosity of this reconstituted milk, measured at 60 rpm (revolutions per minute), at 37° C., is between 25 and 45 cP (S61 spindle) at a pH close to neutrality, and between 130 and 225 cP for a pH range of from 5.5 to 3.5. The reconstituted liquid milk contains 0.52% of pectins and 0.091% of xanthan in the feeding bottle.

Example 3

Process for Manufacturing a Pasteurized Infant Milk in Powder Form Comprising at Least i) One Amidated and Weakly Esterified Pectin, ii) One Highly Esterified Pectin and iii) Xanthan The infant milk base comprising 35% of dry extract is prepared by mixing water previously heated to 75° C. with the various ingredients of the infant milk (proteins, amidated and weakly esterified pectins, highly esterified pectins, carbohydrates, xanthan, minerals, vegetable fats, vitamins and growth factors). The pectins are incorporated into the infant milk base kept stirring in order to obtain complete dissolution thereof. The whole mixture is maintained at 75° C. with stirring in a jacketed tank until the homogenizing step. The infant milk base then undergoes double-stage homogenization at 200/40 bar, i.e. a first homogenizing step is carried out at a pressure of 200 bar and the second homogenizing step is carried out at a pressure of 40 bar. The homogenized infant milk base is then pasteurized by heat treatment at approximately 80° C. for 1 to 2 minutes for the purpose of eliminating the bacteriological risks, in particular those linked to *Cronobacter sakazakii*.

The pasteurized infant milk base then undergoes a spraying step carried out at a pressure of 150 bar, which makes it possible to obtain droplets which have a diameter sufficiently small to be dried with air, the temperature of which at the inlet into the chamber is 185° C. and the temperature of which at the outlet of the chamber is 96° C.

The process implemented makes it possible here to obtain a flow rate of 1000 and 2000 kg of powder/hour.

The reconstituted liquid milk (ready for consumption) obtained from this infant milk powder has a dry extract of approximately 13% in the feeding bottle. The viscosity of this reconstituted milk, measured at 60 rpm (revolutions per minute), at 37° C., is between 25 and 45 cP (S61 spindle) at a pH close to neutrality and between 150 and 250 cP for a pH range of from 5.8 to 3.5. The infant milk powder obtained contains 5% of pectins and 0.7% of xanthan. The reconstituted liquid milk in the feeding bottle therefore contains approximately 0.65% of pectins and 0.091% of xanthan.

Example 4

Comparison of the Viscosity of a Reconstituted Milk According to the Invention with the Viscosity of a Milk Thickened by the Addition of Gelopectose®

"Gelopectose®" is an FSMP (Dietary Food for Special Medical Purposes), mainly composed of pectin. The exact composition is the following: pectin (E440), cellulose (E460), silica (E551), maltodextrin, sodium chloride, calcium chloride, and lemon flavouring.

The exact posology and the exact mode of preparation, given by the manufacturer, are recalled below:

Posology: Use Gelopectose® at the dose of 3% to 5% (i.e. 3 to 5 g for 100 ml of water, before reconstitution). For 90 ml of water before reconstitution, use 2 level teaspoons ("cuillères à café") of Gelopectose (see posology memo for the number of teaspoons of Gelopectose according to the various volumes of water).

Posology Memo:
Water: Gelopectose.
90 ml: 2 teaspoons ("cuillères à café").
120 ml: 2-3 teaspoons ("cuillères à café").
150 ml: 3 teaspoons ("cuillères à café").
180 ml: 3-4 teaspoons ("cuillères à café").
210 ml: 4-5 teaspoons ("cuillères à café").
240 ml: 5 teaspoons ("cuillères à café").
270 ml: 5-6 teaspoons ("cuillères à café").
300 ml: 6 teaspoons ("cuillères à café").

Mode of Administration:
Pour the recommended amount of Gelopectose into a feeding bottle of very hot reconstituted milk (50 to 60° C.). Stir vigorously for approximately 30 seconds, then leave to stand until the gel and the desired temperature for administering it to the infant are obtained.

Above all, do not reshake the feeding bottle after obtaining the gel.

Use water with a low mineral content, recommended for preparing feeding bottles.

The feeding bottle can be stored in a refrigerator (+4° C.) for a maximum of 24 hours; for use, reheat it in a water bath without shaking it."

The objective of the study is to compare the viscosity of an anti-regurgitation infant milk (comprising a hydrolysate of slightly hydrolysed serum proteins) prepared according to the present invention and of a hypoallergenic (HA) infant milk (also comprising a hydrolysate of slightly hydrolysed serum proteins) to which the "Gelopectose®" product has been added.

Method and Tools:
The two products are reconstituted, in a beaker, by mixing with water at 37° C. The reconstitution level is 13%, i.e. 13 g of powder in 90 ml of water. 300 ml of each solution are prepared.

The HA product is reconstituted first, and then heated to 60° C. as indicated by the manufacturer of Gelopectose®. Six teaspoons ("cuillères à café") of Gelopectose® are then added to the 300 ml of milk present in the feeding bottle.

Vigorous shaking of the feeding bottle is required in order to obtain correct dissolution in the feeding bottle and to prevent the formation of lumps. The feeding bottle is then cooled to 37° C.

The anti-regurgitation infant milk according to the invention is reconstituted directly by mixing with water at 37° C.

The viscosities of the two products are then measured using a Brookfield viscometer (DV-I Prime) at the reconstitution pH (close to neutrality) with an S61 spindle at 60 rpm (revolutions per minute) and at a temperature of 37° C.

Hydrochloric acid, with a molarity equal to 1 (1M HCl) is then added to the two reconstituted products so as to achieve a pH of 3.5. The viscosities of the two acidified products are then measured at 37° C. and at a speed of 60 rpm. An S62 spindle was used to measure that of the infant milk according to the invention and an S61 spindle to measure that of the HA milk thickened with Gelopectose®. This is because, since the infant milk prepared according to the present invention has a high viscosity (cf. results below) at acid pH, it was necessary to change the spindle in order to be able to carry out the measurement.

The measurements obtained appear in Table 2 below.

TABLE 2

| | Viscosities in cP | |
|---|---|---|
| | Invention | HA with "Gelopectose ®" |
| pH = approximately 7 | 44 | 90 |
| pH = 3.5 | 225 | 60 |

Conclusion

The anti-regurgitation infant milk according to the present invention demonstrates a much better behaviour, as an anti-regurgitation formula, than the HA formula thickened with the Gelopectose® product.

Indeed, it can be seen that the viscosity of the infant milk prepared according to the present invention increases at acid pH, whereas the viscosity of the HA product with Gelopectose® decreases and attains a low viscosity (see FIG. 1).

Furthermore, the infant milk prepared according to the present invention is simpler and quicker to use since it does not require heating the feeding bottle to 60° C. and leaving it to cool before giving it to the baby.

It should be noted, moreover, that this need to heat the reconstituted infant milk before adding the Gelopectose leads to a destruction of the vitamins. This destruction is avoided with the infant milk according to the invention, which simply needs to be diluted, at 37° C., in water.

Finally, the infant milk prepared according to the present invention shows a low viscosity at a pH close to neutrality, which facilitates the feeding by the baby, whereas, conversely, the milk thickened with Gelopectose® is already very viscous at neutral pH and therefore difficult for the baby to drink.

Example 5

Comparison of the Viscosity of a Reconstituted Milk Comprising a Milk in Powder Form According to the Invention Obtained by Dry Mixing with the Viscosity of a Conventional AR Milk An infant milk base as described in the "infant base" part of the present invention is prepared and collected in powder form at the outlet of a spray tower. 4% of amidated and weakly esterified pectin, 1% of highly esterified pectin and 0.7% of xanthan are then added to this powder base by dry mixing.

Method and Tools:

The liquid infant milk is then prepared, by dilution of the infant milk in powder form according to the invention in hot water (at 60° C.) at 13% of dry extract. Said liquid infant milk is then cooled to 37° C.

The starch-based conventional AR milk is also prepared by diluting the product in water (also at 37° C.) at 13% of dry extract.

The viscosities of the two products are then measured using a Brookfield viscometer (DV-I Prime) at the reconstitution pH (close to neutrality) with an S61 spindle at 60 rpm (revolutions per minute) and at a temperature of 37° C.

Hydrochloric acid, with a molarity equal to 1 (1M HCl), is added to the two reconstituted products so as to achieve a pH of 5.5. The viscosities of the two acidified products are then measured at 37° C. and at a speed of 60 rpm.

Hydrochloric acid, with a molarity equal to 1 (1M HCl), is then again added to the two reconstituted products so as to achieve a pH of 3.5. The viscosities of the two acidified products are then again measured at 37° C. and at a speed of 60 rpm.

TABLE 3

| AR Products | Viscosities in cP | | |
|---|---|---|---|
| | Neutral pH | pH = 5.5 | pH = 3.5 |
| Conventional AR (native proteins) | 10 | 96 | 241 |
| Infant milk according to the invention obtained by dry mixing (native proteins) | 24 | 236 | 234 |

Example 6

Comparison of the Viscosity of a Milk Reconstituted from a Milk in Powder Form According to the Invention Comprising at Least One Weakly Esterified Pectin and One of the Thickeners Chosen from Xanthan, Methylcellulose, Carboxymethylcellulose, Hydroxypropylcellulose, Hydroxypropylmethylcellulose and Guar (Compositions 1 to 8) and of Milks Reconstituted from Milks in Powder Form Comprising "Native" Carob (Compositions 9 and 10) or "Cold-Soluble" Carob (Composition 11)

The objective of the study is to compare the viscosity of anti-regurgitation infant milks comprising a hydrolysate of slightly hydrolysed serum proteins prepared according to the present invention (compositions 1 to 8) and of infant milks also comprising a hydrolysate of slightly hydrolysed serum proteins and "native" carob (compositions 9 and 10) or cold-soluble carob (composition 11).

Method and Tools:

The products according to the invention are prepared without dry addition (compositions 1 to 9). Composition 10 is prepared according to Example 2 of patent application FR 2 913 857. Composition 11 is prepared by drying of an infant milk base and dry addition of 4% of cold-soluble carob.

All the products are reconstituted, in a beaker, by mixing with water at 37° C. The level of reconstitution is 13%, i.e. 13 g of powder in 90 ml of water. 300 ml of each solution are prepared.

The viscosities of the products are then measured using a Brookfield viscometer (DV-I Prime) at the reconstitution pH (close to neutrality) with an S61 spindle (low viscosities) at 60 rpm (revolutions per minute) and at a temperature of 37° C.

Hydrochloric acid, with a molarity equal to 1 (1M HCl), is then added to the reconstituted products so as to achieve a pH of 3.5. The viscosities of the acidified products are then measured at 37° C. and at a speed of 60 rpm. An S62 spindle (high viscosities) was used to measure that of the infant milks of the invention and of composition 11 and an S61 spindle (low viscosities) was used to measure that of the milks of compositions 9 and 10.

Compositions:

| | | Composition 1 according to the invention For 100 g of powder | Composition 2 according to the invention For 100 g of powder |
|---|---|---|---|
| Proteins | g | 12.1 | 12.1 |
| Lipids, of which: | g | 26.2 | 26.2 |
| Linoleic acid | g | 4.5 | 4.5 |
| α-Linolenic acid | mg | 450 | 450 |

-continued

| | | Composition 1 | Composition 2 |
|---|---|---|---|
| Carbohydrates, of which: | g | 52.7 | 52.7 |
| Maltodextrins | g | 46.85 | 44.75 |
| Lactose | g | 0 | 0 |
| Starch | g | 0.94 | 0.94 |
| HM Pectin | g | 1.00 | 3.00 |
| LM amidated pectin | g | 4.00 | 4.00 |
| Xanthan | g | 0.70 | |
| Methylcellulose | g | | 0.80 |
| Energy | kcal | 495.90 | 495.90 |
| Minerals, of which: | g | 4.4 | 4.4 |
| Sodium | mg | 230 | 230 |
| Potassium | mg | 610 | 610 |
| Chlorine | mg | 340 | 340 |
| Calcium | mg | 620 | 620 |
| Phosphorus | mg | 340 | 340 |
| Magnesium | mg | 50 | 50 |
| Iron | mg | 6 | 6 |
| Zinc | mg | 4 | 4 |
| Iodine | µg | 70 | 70 |
| Copper | µg | 350 | 350 |
| Manganese | µg | 50 | 50 |
| Selenium | µg | 10 | 10 |
| Molybdenum | µg | <45 | <45 |
| Chromium | µg | <45 | <45 |
| Fluorine | µg | <980 | <980 |
| Mixture of vitamins | g | 0.3 | 0.3 |

| | | Composition 3 according to the invention For 100 g for powder | Composition 4 according to the invention For 100 g of powder |
|---|---|---|---|
| Proteins | g | 12.1 | 12.1 |
| Lipids, of which: | g | 26.2 | 26.2 |
| Linoleic acid | g | 4.5 | 4.5 |
| α-Linolenic acid | mg | 450 | 450 |
| Carbohydrates, of which: | g | 52.7 | 52.7 |
| Maltodextrins | g | 46.35 | 44.05 |
| Lactose | g | 0 | 0 |
| Starch | g | 0.94 | 0.94 |
| HM Pectin | g | 1.0 | 2.00 |
| LM amidated pectin | g | 4.20 | 4.0 |
| Carboxymethylcellulose | g | 1.00 | |
| Hydroxypropylmethylcellulose | g | | 2.50 |
| Energy | kcal | 495.90 | 495.90 |
| Minerals, of which: | g | 4.4 | 4.4 |
| Sodium | mg | 230 | 230 |
| Potassium | mg | 610 | 610 |
| Chlorine | mg | 340 | 340 |
| Calcium | mg | 620 | 620 |
| Phosphorus | mg | 340 | 340 |
| Magnesium | mg | 50 | 50 |
| Iron | mg | 6 | 6 |
| Zinc | mg | 4 | 4 |
| Iodine | µg | 70 | 70 |
| Copper | µg | 350 | 350 |
| Manganese | µg | 50 | 50 |
| Selenium | µg | 10 | 10 |
| Molybdenum | µg | <45 | <45 |
| Chromium | µg | <45 | <45 |
| Fluorine | µg | <980 | <980 |
| Mixture of vitamins | g | 0.3 | 0.3 |

| | | Composition 5 according to the invention For 100 g of powder | Composition 6 according to the invention For 100 g of powder |
|---|---|---|---|
| Proteins | g | 12.1 | 12.1 |
| Lipids, of which: | g | 26.2 | 26.2 |
| Linoleic acid | g | 4.5 | 4.5 |
| α-Linolenic acid | mg | 450 | 450 |
| Carbohydrates, of which: | g | 52.7 | 52.7 |
| Maltodextrins | g | 44.55 | 45.05 |
| Lactose | g | 0 | 0 |
| Starch | g | 0.94 | 0.94 |
| HM Pectin | g | 2.00 | 2.00 |
| LM amidated pectin | g | 4.0 | 4.0 |
| Hydroxypropylcellulose | g | 2.00 | |
| Guar | g | | 1.00 |
| Energy | kcal | 495.90 | 495.9 |
| Minerals, of which: | g | 4.4 | 4.4 |
| Sodium | mg | 230 | 230 |
| Potassium | mg | 610 | 610 |
| Chlorine | mg | 340 | 340 |
| Calcium | mg | 620 | 620 |
| Phosphorus | mg | 340 | 340 |
| Magnesium | mg | 50 | 50 |
| Iron | mg | 6 | 6 |
| Zinc | mg | 4 | 4 |
| Iodine | µg | 70 | 70 |
| Copper | µg | 350 | 350 |
| Manganese | µg | 50 | 50 |
| Selenium | µg | 10 | 10 |
| Molybdenum | µg | <45 | <45 |
| Chromium | µg | <45 | <45 |
| Fluorine | µg | <980 | <980 |
| Mixture of vitamins | g | 0.3 | 0.3 |

| | | Composition 7 according to the invention For 100 g of powder | Composition 8 according to the invention For 100 g of powder |
|---|---|---|---|
| Proteins | G | 12.1 | 12.1 |
| Lipids, of which: | G | 26.2 | 26.2 |
| Linoleic acid | G | 4.5 | 4.5 |
| α-Linolenic acid | mg | 450 | 450 |
| Carbohydrates, of which: | g | 52.7 | 52.7 |
| Maltodextrins | g | 44.55 | 45.05 |
| Lactose | g | 0 | 0 |
| Starch | g | 0.94 | 0.94 |
| HM Pectin | g | | 2.00 |
| LM pectin | g | 4.0 | 4.0 |
| Xanthan | g | 1.00 | 1.00 |
| Energy | kcal | 495.90 | 495.9 |
| Minerals, of which: | g | 4.4 | 4.4 |
| Sodium | mg | 230 | 230 |
| Potassium | mg | 610 | 610 |
| Chlorine | mg | 340 | 340 |
| Calcium | mg | 620 | 620 |
| Phosphorus | mg | 340 | 340 |
| Magnesium | mg | 50 | 50 |
| Iron | mg | 6 | 6 |
| Zinc | mg | 4 | 4 |
| Iodine | µg | 70 | 70 |
| Copper | µg | 350 | 350 |
| Manganese | µg | 50 | 50 |
| Selenium | µg | 10 | 10 |
| Molybdenum | µg | <45 | <45 |
| Chromium | µg | <45 | <45 |
| Fluorine | µg | <980 | <980 |
| Mixture of vitamins | g | 0.3 | 0.3 |

| | | Composition 9 For 100 g of powder | Composition 10 (according to Example 2 of patent application FR 2 913 857) For 100 g of powder |
|---|---|---|---|
| Proteins | g | 12.1 | 12.1 |
| Lipids, of which: | g | 26.2 | 26.2 |
| Linoleic acid | g | 4.5 | 4.5 |
| α-Linolenic acid | mg | 450 | 450 |
| Carbohydrates, of which: | g | 52.7 | 52.7 |

-continued

| | | | |
|---|---|---|---|
| Maltodextrins | g | 44.55 | 46.05 |
| Lactose | g | 0 | 0 |
| Starch | g | 0.94 | 0.94 |
| HM Pectin | g | 2.00 | |
| LM amidated pectin | g | 4.0 | |
| Native carob bean gum | | 1.50 | 4.00 |
| Energy | kcal | 495.9 | 495.9 |
| Minerals, of which: | g | 4.4 | 4.4 |
| Sodium | mg | 230 | 230 |
| Potassium | mg | 610 | 610 |
| Chlorine | mg | 340 | 340 |
| Calcium | mg | 620 | 620 |
| Phosphorus | mg | 340 | 340 |
| Magnesium | mg | 50 | 50 |
| Iron | mg | 6 | 6 |
| Zinc | mg | 4 | 4 |
| Iodine | µg | 70 | 70 |
| Copper | µg | 350 | 350 |
| Manganese | µg | 50 | 50 |
| Selenium | µg | 10 | 10 |
| Molybdenum | µg | <45 | <45 |
| Chromium | µg | <45 | <45 |
| Fluorine | µg | <980 | <980 |
| Mixture of vitamins | g | 0.3 | 0.3 |

| | Composition 11 For 100 g of powder | |
|---|---|---|
| Proteins | g | 12.1 |
| Lipids, of which: | g | 26.2 |
| Linoleic acid | g | 4.5 |
| α-Linolenic acid | mg | 450 |
| Carbohydrates, of which: | g | 52.7 |
| Maltodextrins | g | 46.05 |
| Lactose | g | 0 |
| Starch | g | 0.94 |
| Cold-soluble carob bean gum | g | 4.00 |
| Energy | kcal | 495.9 |
| Minerals, of which: | g | 4.4 |
| Sodium | mg | 230 |
| Potassium | mg | 610 |
| Chlorine | mg | 340 |
| Calcium | mg | 620 |
| Phosphorus | mg | 340 |
| Magnesium | mg | 50 |
| Iron | mg | 6 |
| Zinc | mg | 4 |
| Iodine | µg | 70 |
| Copper | µg | 350 |
| Manganese | µg | 50 |
| Selenium | µg | 10 |
| Molybdenum | µg | <45 |
| Chromium | µg | <45 |
| Fluorine | µg | <980 |
| Mixture of vitamins | g | 0.3 |

Results:

| | Viscosities in cP | | | | | | | | | | |
|---|---|---|---|---|---|---|---|---|---|---|---|
| Compositions | 1 | 2 | 3 | 4 | 5 | 6 | 7 | 8 | 9 | 10 | 11 |
| pH = 6.7 | 44 | 24 | 29 | 17 | 38 | 40 | 50 | 48 | 60 | 4 | 74 |
| pH = 3.5 | 225 | 162 | 195 | 158 | 174 | 155 | 152 | 165 | 17 | 25 | 200 |

Conclusion:

The anti-regurgitation infant milks according to the present invention (compositions 1 to 8) demonstrate a much better behaviour, as an anti-regurgitation formula, than the products of compositions 9 and 10. The product of composition 11 gives good results, but has the drawback of having to add cold-soluble carob to the rest of the infant base by dry mixing, such an operation significantly increasing the microbiological risk.

Thus, it can be seen that the viscosity of the infant milks prepared according to the present invention (compositions 1 to 8) increases at acid pH, whereas the viscosity of the products of compositions 9 and 10 decreases and the reconstituted products rapidly undergo phase separation (cf. viscosities of compositions 9 and 10 at pH 3.5). These compositions are not therefore suitable for use in reducing regurgitations and/or reflux in infants and cannot be used as anti-regurgitation and/or anti-reflux compositions for the purposes of the present invention.

We claim:

1. An anti-reflux and/or anti-regurgitation infant milk in powder form comprising at least one weakly esterified pectin and at least one thickener and/or gelling agent chosen from xanthan gum, carboxymethylcellulose, hydroxypropylcellulose, hydroxymethylcellulose, methylcellulose, hydroxylpropylmethylcellulose or guar gum.

2. The infant milk according to claim 1, wherein said composition further comprises a protein fraction that contains a majority of hydrolysed proteins and/or of amino acids as a mixture.

3. The infant milk according to claim 1, wherein said composition comprises at least one highly esterified pectin.

4. The infant milk according to claim 1, wherein said composition comprises for 100 grams of dry matter, 0.5 to 10 grams of pectin and 0.5 to 4 grams of the chosen thickener.

5. The infant milk according to claim 4, wherein the chosen thickener is xanthan gum.

6. An anti-reflux and/or anti-regurgitation infant milk reconstituted from the anti-reflux and/or anti-regurgitation infant milk in powder form according to claim 1, wherein it is liquid at pH 7 and viscous at a pH between 6 and 3.5.

7. The reconstituted infant milk according to claim 6, wherein the viscosity of said milk, at a pH between 5.5 and 3.5, is between 200 centipoises and 300 centipoises.

8. An anti-reflux and/or anti-regurgitation infant milk reconstituted from the anti-reflux and/or anti-regurgitation infant milk in powder form according to claim 6, wherein it is liquid at pH 7 and viscous at a pH between 5.8 and 5.

9. The infant milk according to claim 1, wherein said at least one weakly esterified pectin is an amidated and weakly esterified pectin.

* * * * *

UNITED STATES PATENT AND TRADEMARK OFFICE
CERTIFICATE OF CORRECTION

PATENT NO. : 9,278,110 B2
APPLICATION NO. : 14/672619
DATED : March 8, 2016
INVENTOR(S) : Margossian et al.

Page 1 of 1

It is certified that error appears in the above-identified patent and that said Letters Patent is hereby corrected as shown below:

In the Specification

Column 19,
Line 60, "teaspoons of Gel opectose" should read --teaspoons of Gelopectose--.

In the Claims

Column 26,
Lines 24-25, "hydroxylpropylmethylcellulose" should read --hydroxypropylmethylcellulose--.

Signed and Sealed this
Fourteenth Day of June, 2016

Michelle K. Lee
*Director of the United States Patent and Trademark Office*